United States Patent
Schüle

(10) Patent No.: US 7,836,532 B2
(45) Date of Patent: Nov. 23, 2010

(54) METHOD AND APPARATUS FOR ATTACHING ACCESSORIES TO A SURGICAL FIXTURE

(75) Inventor: Edgar Franz Schüle, Freiburg (DE)

(73) Assignee: pro med instruments GmbH, Freiburg (DE)

( * ) Notice: Subject to any disclaimer, the term of this patent is extended or adjusted under 35 U.S.C. 154(b) by 709 days.

(21) Appl. No.: 11/250,630

(22) Filed: Oct. 14, 2005

(65) Prior Publication Data
US 2006/0084900 A1 Apr. 20, 2006

Related U.S. Application Data

(60) Provisional application No. 60/619,168, filed on Oct. 15, 2004.

(51) Int. Cl.
*A61G 13/12* (2006.01)
(52) U.S. Cl. .................................... 5/622; 5/621; 5/637
(58) Field of Classification Search ............ 5/621–624, 5/637, 640; 248/316.1
See application file for complete search history.

(56) References Cited

U.S. PATENT DOCUMENTS

| | | | |
|---|---|---|---|
| 1,839,726 A | 1/1932 | Arnold | |
| 2,586,488 A | 2/1952 | Smith | |
| 2,594,086 A | 4/1952 | Smith | |
| 3,522,799 A | 8/1970 | Gauthier | |
| 3,835,861 A | 9/1974 | Kees et al. | |
| 4,312,336 A | 1/1982 | Danieletto et al. | |
| 4,392,645 A | 7/1983 | Westphal | |
| 4,457,300 A | 7/1984 | Budde | |
| 4,539,979 A | 9/1985 | Bremer | |
| 4,541,421 A | 9/1985 | Iversen et al. | |
| 4,543,947 A | 10/1985 | Blackstone | |

(Continued)

FOREIGN PATENT DOCUMENTS

WO WO 97/40764 4/1997

(Continued)

OTHER PUBLICATIONS

Partial European Search Report dated Feb. 6, 2006 for European Patent Application No. EP 05292169.9, filed Oct. 14, 2005.

(Continued)

*Primary Examiner*—Fredrick Conley
(74) *Attorney, Agent, or Firm*—Frost Brown Todd LLC

(57) ABSTRACT

A surgical fixture includes a skull clamp having a pair of arms. Each of the arms includes a rail having a generally "T"-shaped or dovetail-shaped cross section. An accessory attachment assembly comprises a gripping portion having a pair of jaws that are operable to selectively grip a rail. The accessory attachment assembly also includes a body portion having a feature for receiving surgical accessories. Surgical accessories may be rotated relative to the accessory attachment assembly along a first plane, and may further be secured to the accessory attachment assembly. The body portion may be rotated relative to gripping portion along a second plane. A mechanism is operable to simultaneously effect gripping with the jaws while preventing rotation of the body portion relative to the gripping portion. The mechanism is also operable to simultaneously release gripping of the jaws while permitting rotation of the body portion relative to the gripping portion.

21 Claims, 10 Drawing Sheets

U.S. PATENT DOCUMENTS

| | | | |
|---|---|---|---|
| 4,615,072 | A | 10/1986 | Lautenschlager, Jr. |
| 4,667,660 | A | 5/1987 | Eingorn |
| 4,796,846 | A * | 1/1989 | Meier et al. ............... 248/286.1 |
| 4,803,976 | A | 2/1989 | Frigg et al. |
| 4,807,605 | A | 2/1989 | Mattingly |
| 4,827,926 | A | 5/1989 | Carol |
| 4,838,264 | A | 6/1989 | Bremer et al. |
| 4,971,037 | A | 11/1990 | Pelta |
| 5,203,765 | A | 4/1993 | Friddle, Jr. |
| 5,276,927 | A * | 1/1994 | Day ............................. 5/622 |
| 5,284,129 | A | 2/1994 | Agbodoe et al. |
| 5,529,358 | A | 6/1996 | Dinkler et al. |
| 5,537,704 | A | 7/1996 | Dinkler et al. |
| 5,630,805 | A | 5/1997 | Ternamian |
| 5,722,978 | A | 3/1998 | Jenkins, Jr. |
| 5,865,780 | A | 2/1999 | Tuite |
| 5,891,157 | A | 4/1999 | Day et al. |
| 6,110,182 | A | 8/2000 | Mowlai-Ashtiani |
| 6,129,729 | A | 10/2000 | Snyder |
| 6,198,961 | B1 | 3/2001 | Stern et al. |
| 6,306,146 | B1 | 10/2001 | Dinkler |
| 6,598,275 | B1 * | 7/2003 | Kolody et al. ................. 24/455 |
| 6,659,972 | B2 | 12/2003 | Stamper et al. |
| 7,232,411 | B2 | 6/2007 | Dinkler, II et al. |
| 2001/0029379 | A1 | 10/2001 | Grotehuis |
| 2003/0149429 | A1 | 8/2003 | Ferrante et al. |

FOREIGN PATENT DOCUMENTS

| | | |
|---|---|---|
| WO | WO 02/085187 | 10/2002 |

OTHER PUBLICATIONS

EPO Search Report dated May 11, 2006 for Application EP05292169 filed Oct. 14, 2005.

(Author Unknown); "Bookwalter Retractor Kit II"; Codman.

Screenshots from www.integra-ls.com, printed Jan. 28, 2005.

Screenshots from www.bicakcilar.com, printed Jan. 28, 2005.

(Author Unknown); "Accessories"; Officing Sordina S.p.A.

Screenshots from www.integra-ls.com, printed Dec. 8, 2005.

Tuite, Gerald F., M.D. et al., Abstract "Use of an Adjustable Transportable Radiolucent Spinal Immobilization Device in the Comprehensive Management of Cervical Spine Instability, J. Of Neurosurgery," vol. 85(6) (Dec. 1996) American Assoc. Of Neurosurgeons.

\* cited by examiner

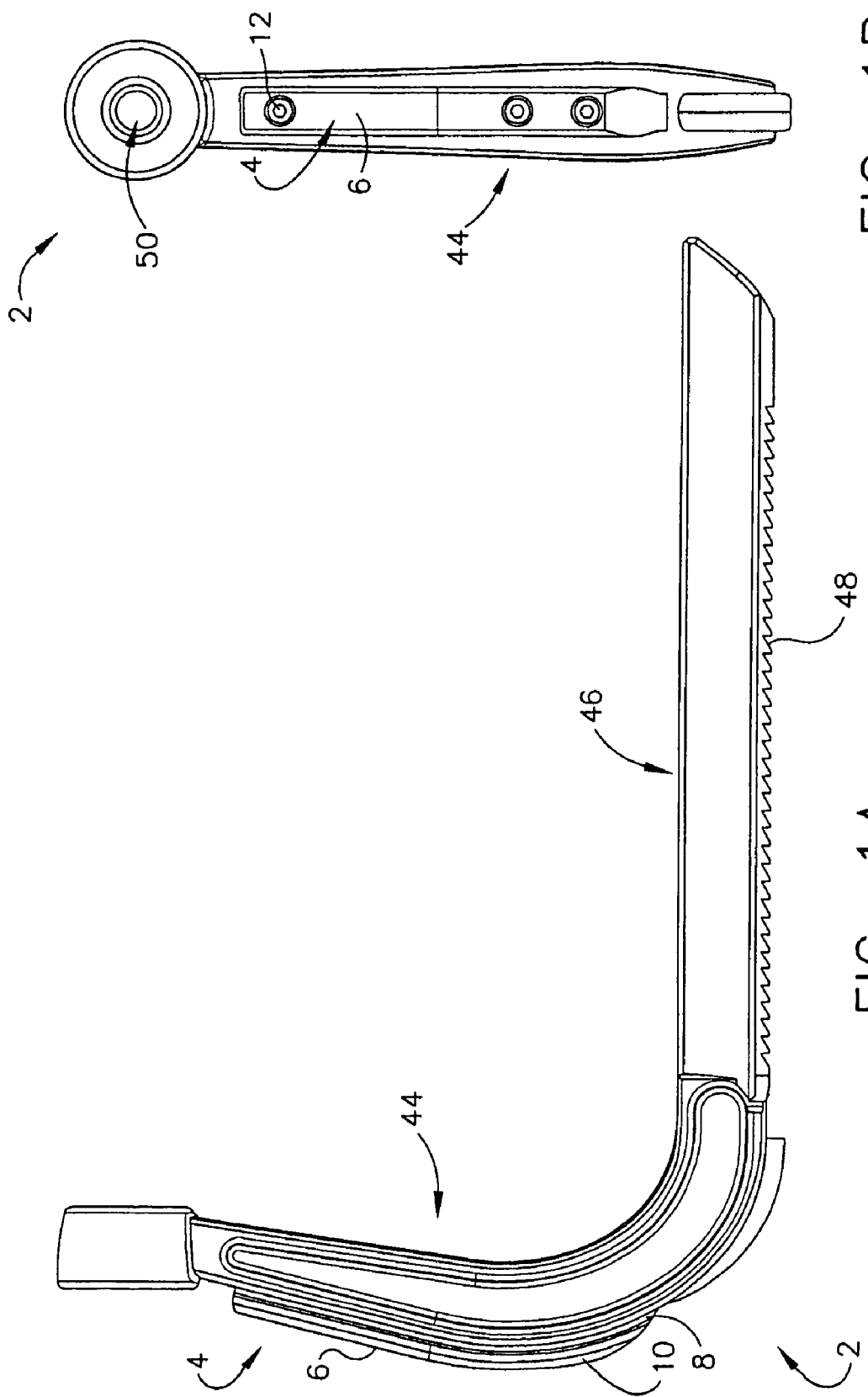

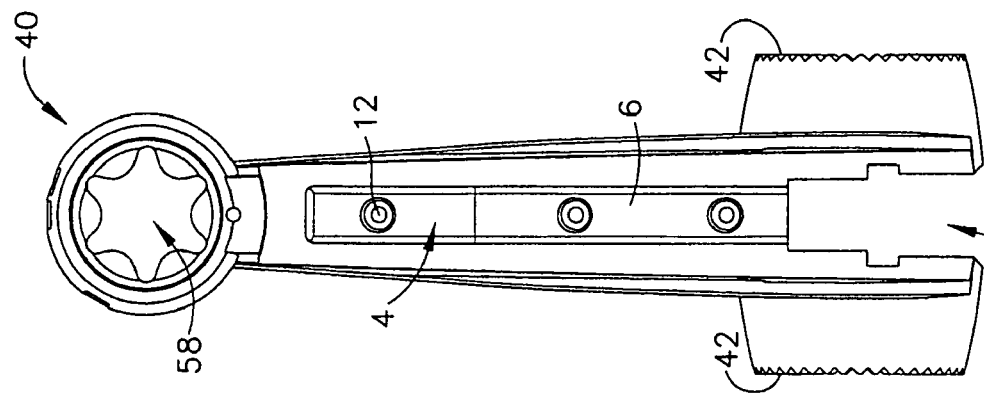
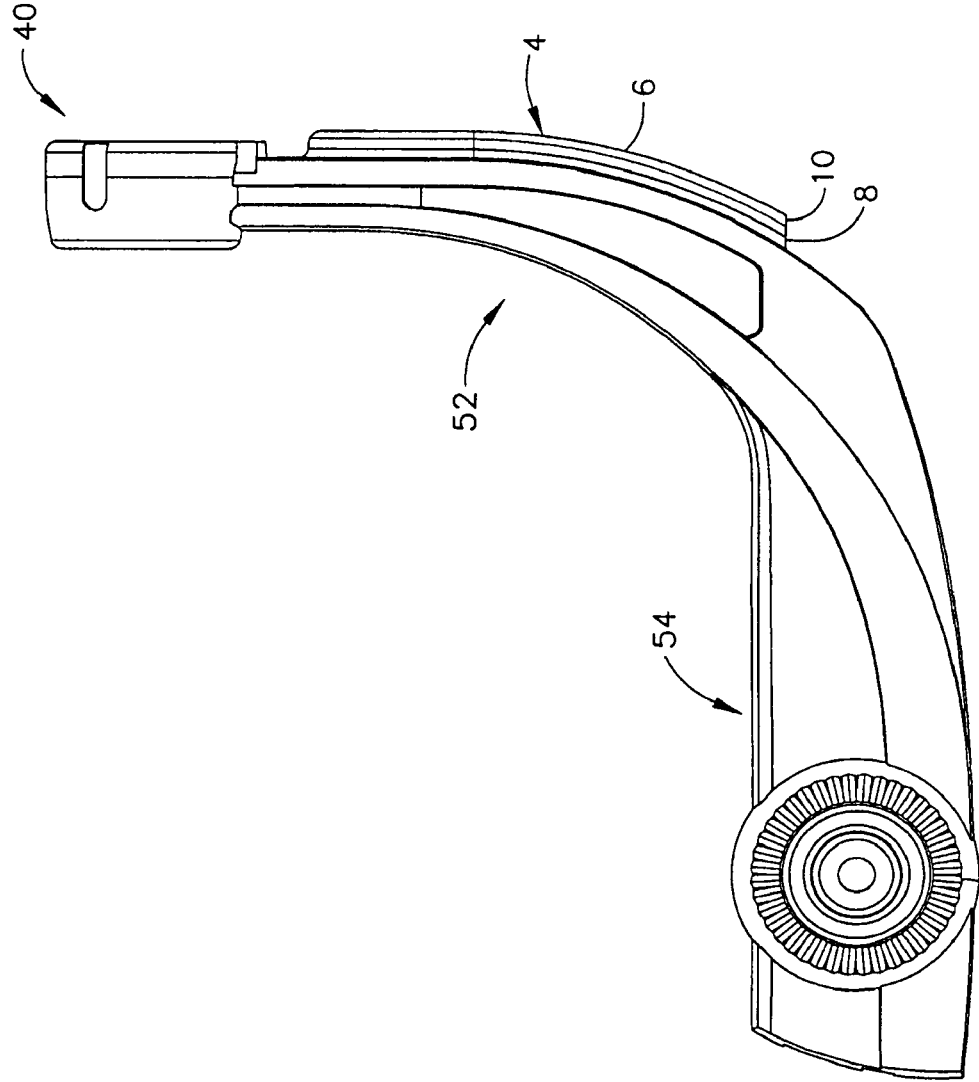

METHOD AND APPARATUS FOR ATTACHING ACCESSORIES TO A SURGICAL FIXTURE

PRIORITY

This application claims priority from the disclosure of U.S. Provisional Patent Application Ser. No. 60/619,168, entitled "Method and Apparatus for Attaching Accessories to a Surgical Fixture," filed Oct. 15, 2004, the disclosure of which is incorporated by reference herein.

BACKGROUND OF THE INVENTION

During surgical operations or other procedures, a portion of the body upon which surgery is being conducted may be substantially immobilized, such as, for example, a patient's head during head or neck surgery. Such immobilization of a patient's head, for example, may be accomplished with a fixture such as a skull clamp or other fixture. It may be desirable to have one or more surgical accessories or additional fixtures securely attached or mounted close at hand during surgery. In some circumstances, it may be desirable and convenient to have such accessories or fixtures mounted directly to the fixture used for immobilization. In addition, it may be desirable to permit the selective attachment and/or adjustment of such accessories or fixtures. Of course, such features are not required, and one may be obtained without necessarily obtaining another. While many accessories and fixtures exist, it is believed that no one prior to the inventors has created or used the invention described in the appended claims.

BRIEF DESCRIPTION OF THE DRAWINGS

While the specification concludes with claims that particularly point out and distinctly claim the invention, it is believed the expressly disclosed exemplary embodiments of the present invention can be understood from the following description taken in conjunction with the accompanying drawings, in which like reference numerals identify the same elements. The drawings and detailed description which follow are intended to be merely illustrative of the expressly disclosed exemplary embodiments and are not intended to limit the scope of the invention as set forth in the appended claims. In the drawings:

FIG. 1A depicts a side view of a skull clamp extension first arm having a rail;

FIG. 1B depicts an end view of the arm of FIG. 1B;

FIG. 2A depicts a side view of a skull clamp extension second arm having a rail;

FIG. 2B depicts an end view of the arm of FIG. 2A;

Figure 3A:
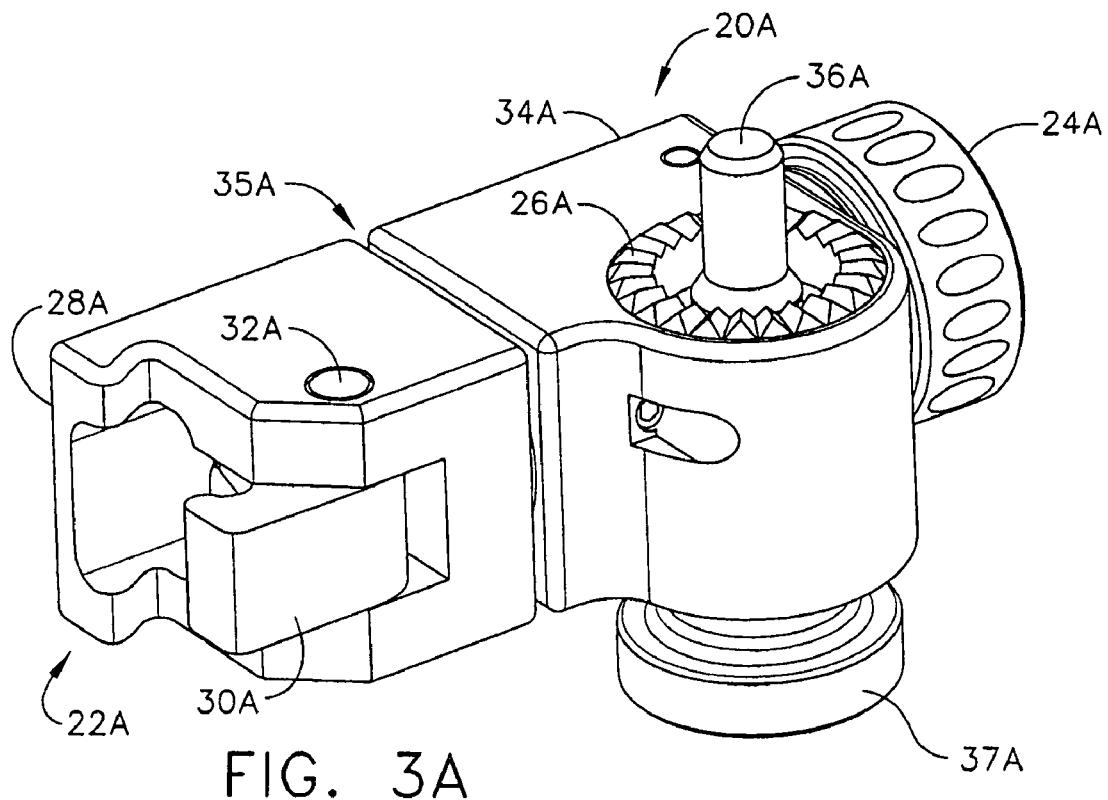
FIG. 3A depicts a perspective view of an attachment assembly.
Figure 3B:
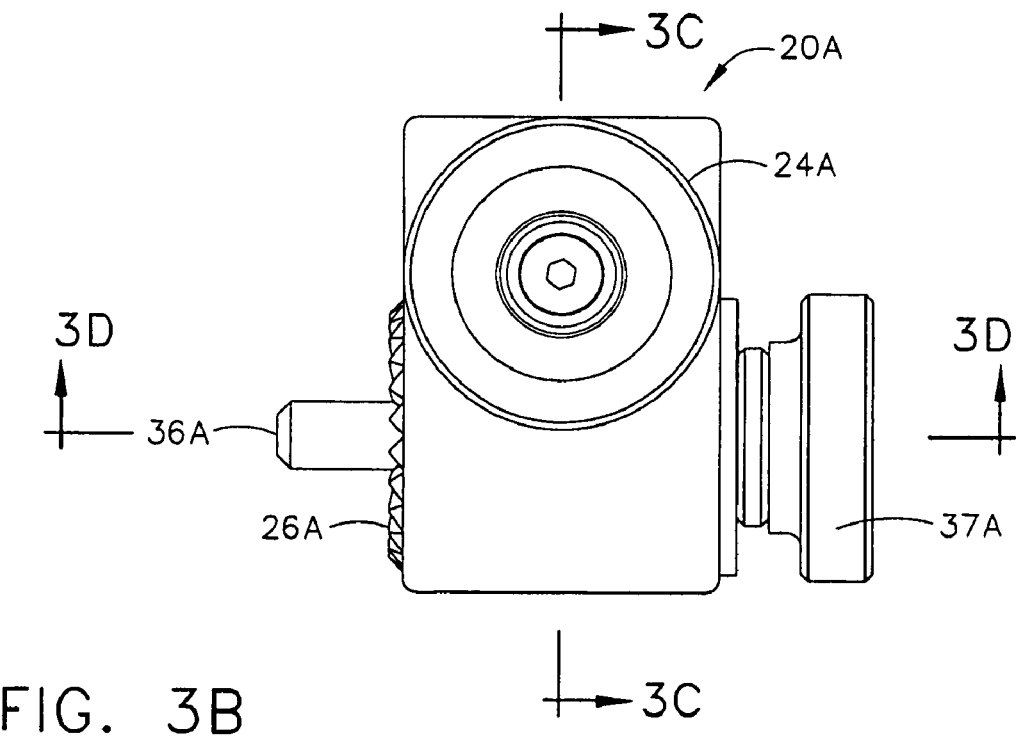
FIG. 3B depicts an end view of the assembly of FIG. 3A.
Figure 3C:
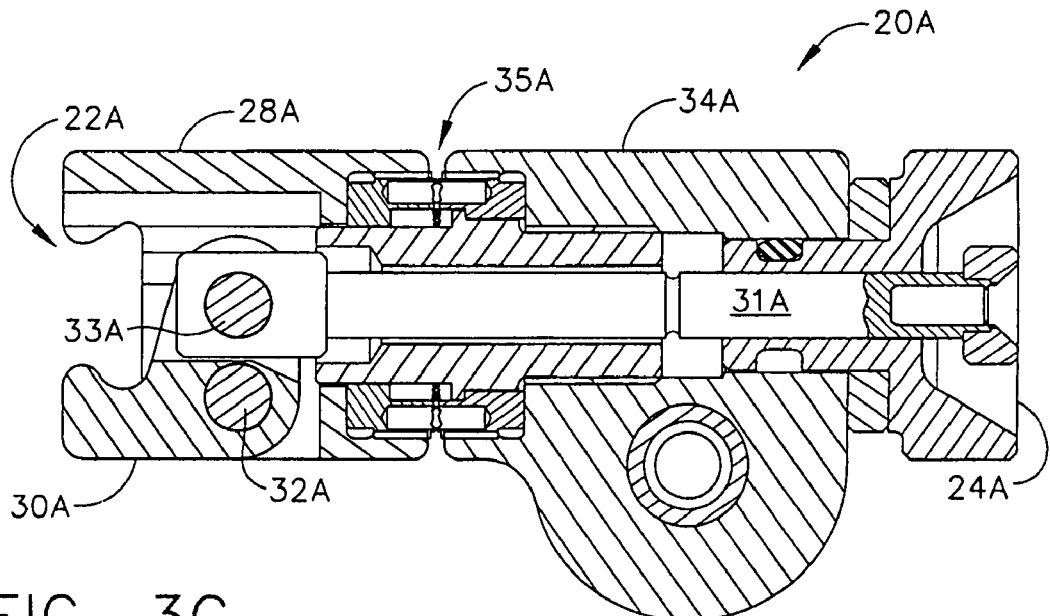
FIG. 3C depicts a cross-sectional view of the assembly of FIG. 3A, taken along line 3C of FIG. 3B.
Figure 3D:
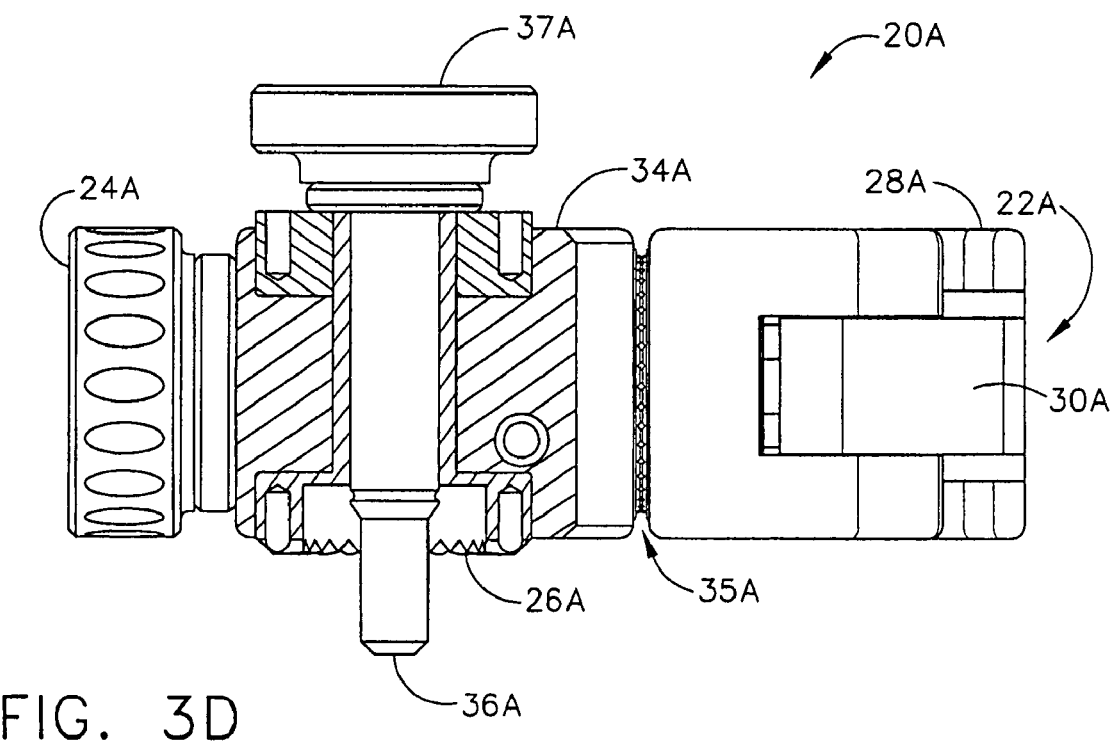
FIG. 3D depicts a cross-sectional view of the assembly of FIG. 3A, taken along line 3D of FIG. 3B.
Figure 4A:
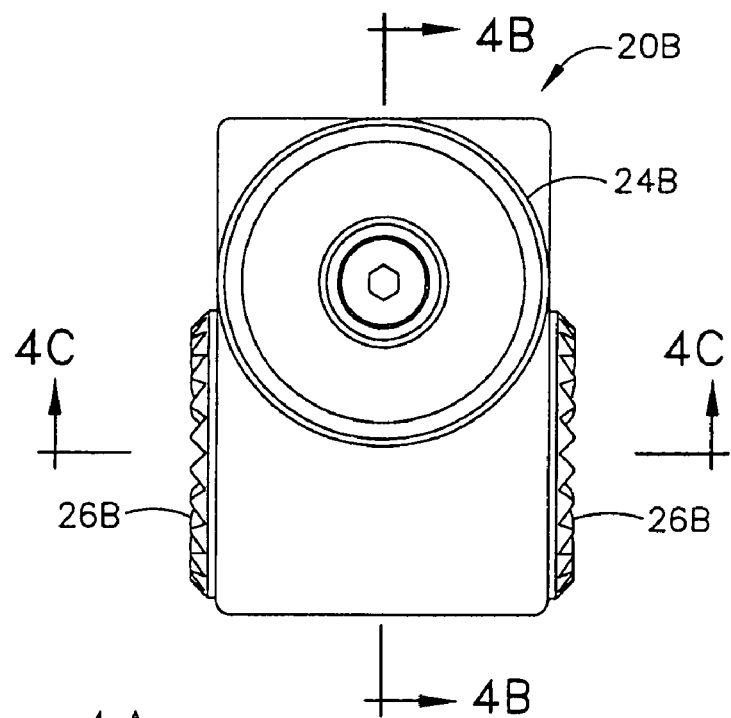
FIG. 4A depicts and end view of an alternative attachment assembly.
Figure 4B:
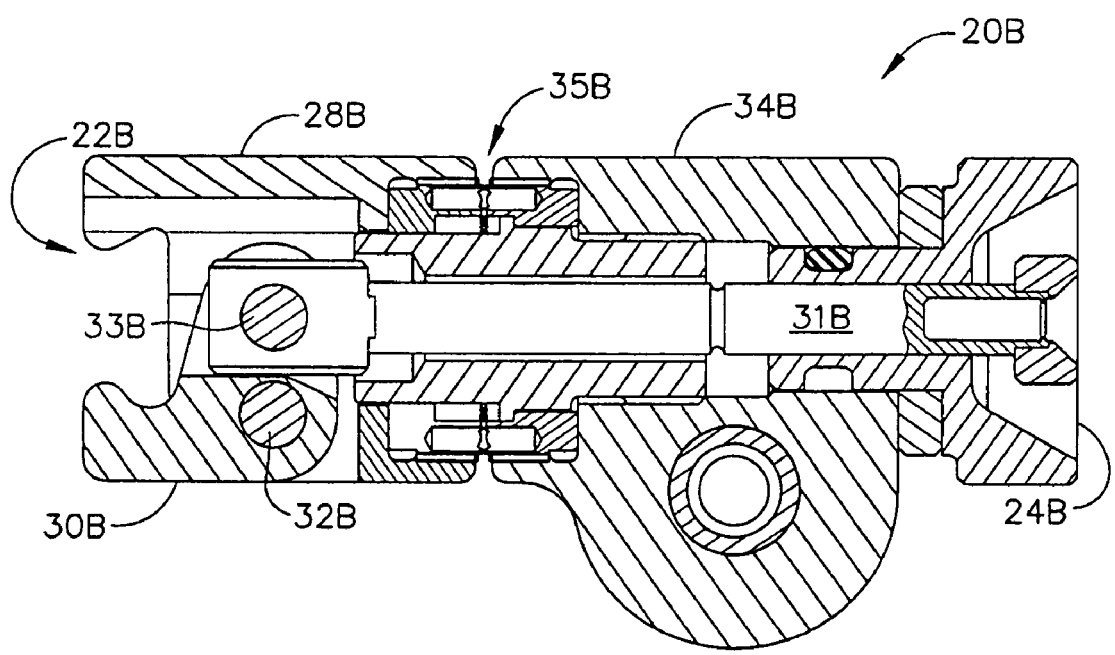
FIG. 4B depicts a cross-sectional view of the assembly of FIG. 4A, taken along line 4B of FIG. 4A.
Figure 4C:
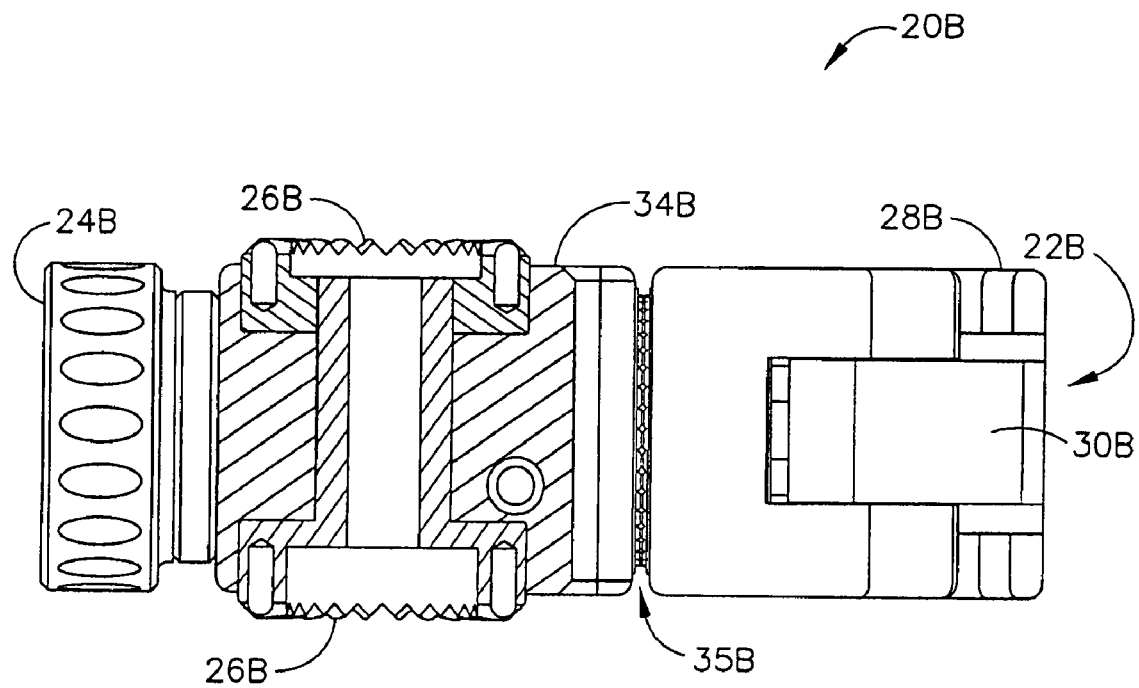
FIG. 4C depicts a cross-sectional view of the assembly of FIG. 4A, taken along line 4C of FIG. 4A.
Figure 5A:
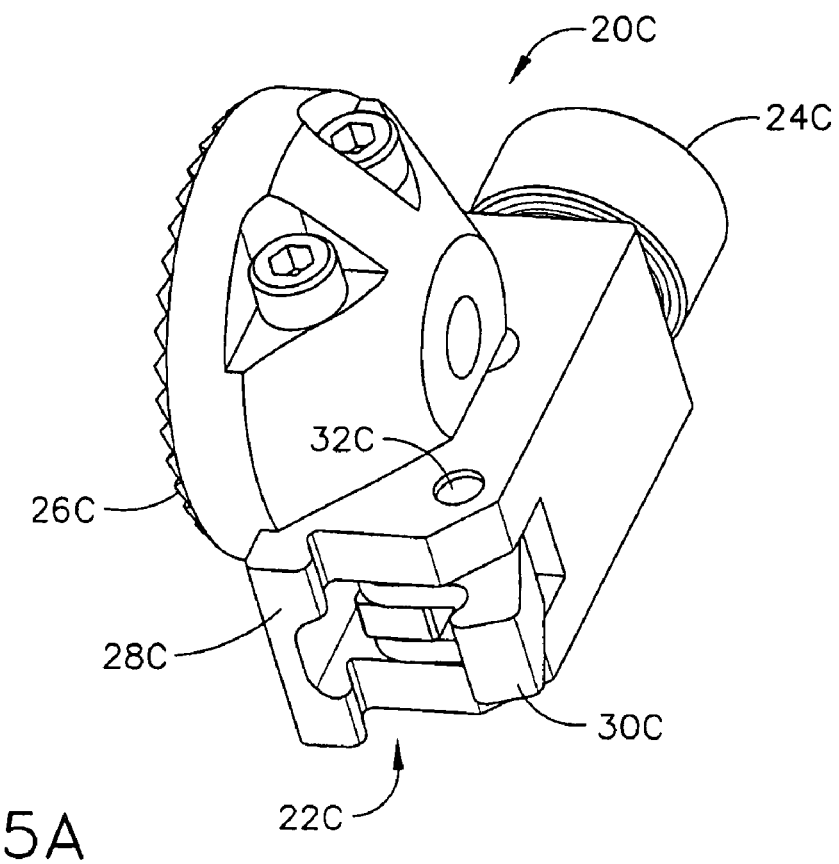
FIG. 5A depicts a perspective view of an alternative attachment assembly.
Figure 5B:
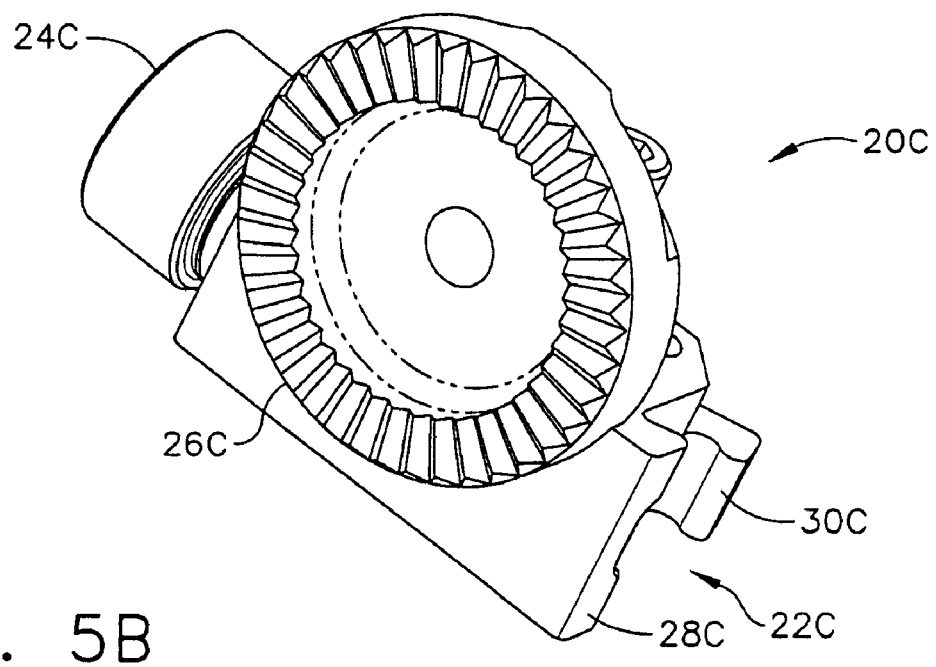
FIG. 5B depicts a perspective view of the assembly of FIG. 5A.
Figure 5C:
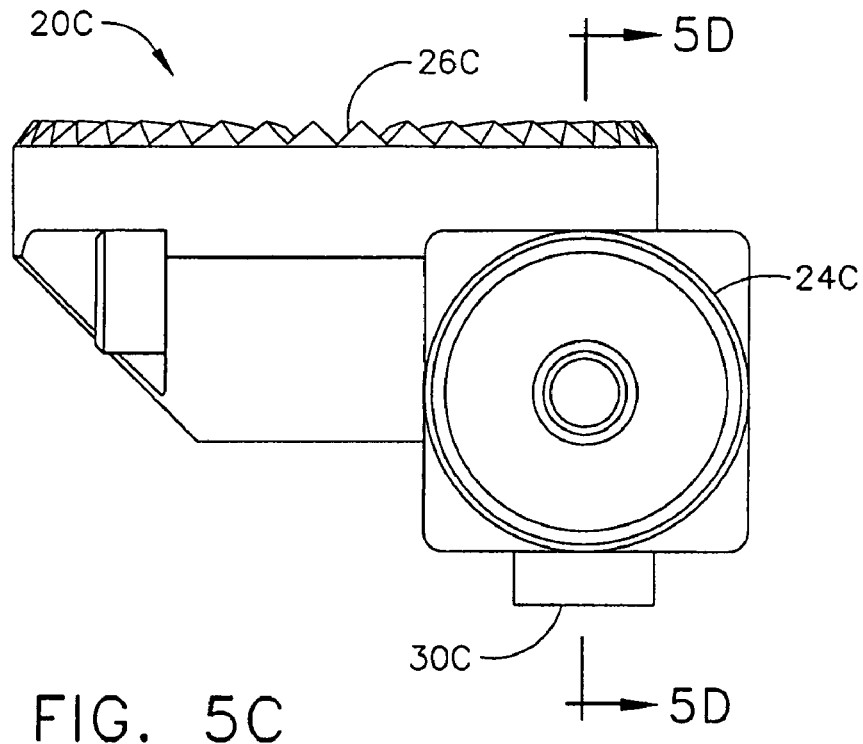
FIG. 5C depicts an end view of the assembly of FIG. 5A.
Figure 5D:
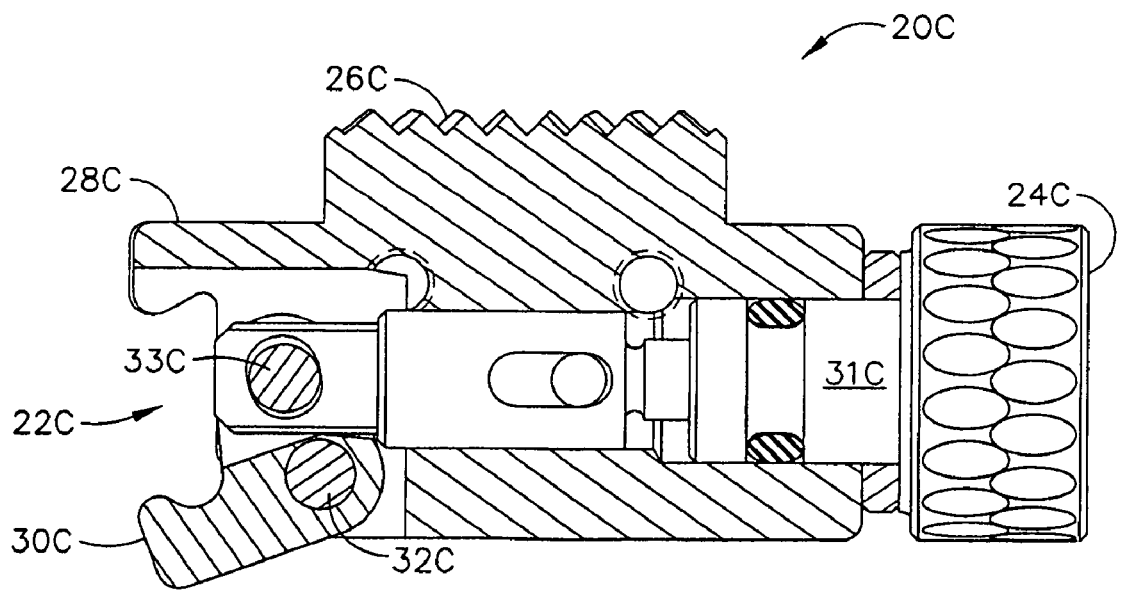
FIG. 5D depicts a cross-sectional view of the assembly of FIG. 5A, taken along line 5D of FIG. 5C.

Reference will now be made in detail to exemplary embodiments of the invention, including the preferred embodiment, an example of which is illustrated in the accompanying drawings.

DETAILED DESCRIPTION OF EMBODIMENTS OF THE INVENTION

The following description should not be used to limit the scope of the present invention. Other examples, features, aspects, embodiments, and advantages of the invention will become apparent to those skilled in the art from the following description, which includes by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive. It should therefore be understood that the inventor contemplates a variety of embodiments that are not explicitly disclosed herein.

FIGS. 1A through 2B depict components of a disassembled exemplary skull clamp. As shown, the skull clamp of this example comprises a first arm (2) and a second arm (40). Arm (2) comprises an insert portion (46) and an upright portion (44). As shown, insert portion (46) is generally perpendicular to upright portion (44). It will be appreciated, however, that any other relative orientation of portions (44, 46) may be used, including but not limited to obtuse angles, acute angles, a plurality of angles, one or more curves, etc. Insert portion (46) comprises a plurality of teeth (48). The end of upright portion (44) comprises an opening (50). Opening (50) is configured to receive a variety of objects, including but not limited to skull pin receiving fixtures (not shown), other cranial stabilizing components, or any other objects.

Arm (40) comprises a receiving portion (54) and an upright portion (52). As shown, receiving portion (54) is generally perpendicular to upright portion (52). It will be appreciated, however, that any other relative orientation of portions (54, 52) may be used, including but not limited to obtuse angles, acute angles, a plurality of angles, one or more curves, etc. The end of upright portion (44) comprises an opening (58). Opening (58) is configured to receive a variety of objects, including but not limited to skull pin receiving fixtures (not shown), other cranial stabilizing components, or any other objects. Receiving portion (54) comprises a recess (56), which is configured to receive insert portion (46) of arm (2). It will be appreciated that recess (56) may be substituted or supplemented with an opening, a slot, or any other feature or configuration, or may be otherwise modified or omitted.

In the present example, arms (2, 40) are configured to form a skull clamp (not shown) when insert portion (46) of arm (2) is inserted in recess (56) of arm (40). Skull clamps are known in the art, and may be used for immobilizing a patient's head during head or neck surgery, by way of example only. Of course, skull clamps may be suitable for other uses. Additionally, other surgical fixtures for immobilizing parts of a patient's body during surgery or for other purposes are known in the art. It will be appreciated that the skull clamp assembly of the present example is merely illustrative, and that features of the present example may be used with any other type of component of a surgical fixture, including accessories for surgical fixtures, as well as with a variety of other fixtures and objects.

With arms (2, 40) positioned to form a skull clamp, it will be appreciated that arm (40) may be used as a base member, and arm (2) adjusted relative to arm (40). In other words, arm (40) may be secured to a stand, table, rail, etc., or other stationary member, and arm (2) may be adjusted relative to arm (40) to create a desired distance between upright portions (44, 52). Upon achieving the desired adjustment of arm (2) relative to arm (40), teeth (48) on insert portion (46) of arm (2) may be used to substantially secure arm (2) relative to arm (40). Of course, arm (2) may alternatively be used as a base member for a skull clamp, and arm (40) may thus be adjusted relative to arm (2). Still other suitable configurations will be apparent to those of ordinary skill in the art.

In the present example, arm (2) further comprises a rail (4), which is secured thereto. A similar rail (4) is secured to arm (40). Each rail (4) comprises an outer surface (6) and a pair of sidewalls (8). In the present example, each sidewall (8) in cross section has a recessed portion to define a longitudinal flange (10) adjacent outer surface (6). In one embodiment, each rail (4) has a generally "T"-shaped or "I"-shaped cross section. In another embodiment, each rail (4) has a generally dovetail-shaped cross section. In yet another embodiment, each rail has a generally mushroom-shaped cross section. Still other suitable cross sections will be apparent to those of ordinary skill in the art.

As shown, each rail (4) is secured to respective arms (2, 40) with screws (12). Of course rail (4) may be secured to arms (2, 40) using any suitable variation of screws (12), including but not limited to bolts, rivets, clamps, adhesives, or other fasteners. Alternatively, arms (2, 40) and rails (4) may be configured to fit such that rails (4) may be secured without the use of a fastener.

As shown, each rail (4) is configured to conform to the profile of respective arm (2, 40). Also as shown, outer surface (6) and longitudinal flange (10) of rail (4) may be substantially parallel with, or may substantially follow, the profile of respective arm (2, 40). However, it will be appreciated by those skilled in the art that outer surface (6) and/or longitudinal flange (10) of rail (4) may alternatively be substantially straight, that rail (4) may extend in length beyond the overall dimensions of corresponding arm (2, 40), or may have any other suitable configuration. When outer surface (6) and longitudinal flange (10) of rail (4) are straight rather than curved as shown in the figures, it will be appreciated that rail (4) may be configured such that an inside surface of rail (4) is still curved to follow the profile of corresponding arm (2, 40). Still other suitable configurations will be apparent to those of ordinary skill in the art.

In yet another embodiment, each rail (4) is separated by a distance from corresponding arm (2, 40), and is secured to corresponding arm (2, 40) via posts or other components, which may be of varying lengths or other dimensions to accommodate the profile of corresponding arm (2, 40) and/or provide for the position in which it is desired that rail (4) be situated with respect to corresponding arm (2, 40). For instance, rail (4), corresponding arm (2, 40), and/or components therebetween may be configured such that the position of each rail (4) relative to corresponding arm (2, 40) is adjustable.

In yet another embodiment, each arm (2, 40) integrally incorporates a corresponding rail (4) (e.g., each arm (2, 40) and corresponding rail (4) are a homogenous continuum of material). For instance, each arm (2, 40) may be cast, machined, and/or molded such that corresponding rail (4) is integrally formed therewith. Still other suitable techniques for constructing arm (2 or 40) with an integrally formed rail (4), or adding rail (4) to an existing arm (2, 40), will be apparent to those of ordinary skill in the art.

It will be appreciated that a rail (4) may be added to any component other than arms (2, 40), including but not limited to other components described herein. In addition, while FIGS. 1A through 2B depict a single rail (4) on each arm (2, 40), it will be appreciated that a plurality of rails (4) may be secured to each arm (2, 40) or to other components. While arms (2, 40) are discussed herein as being produced with rail (4), a rail (4) may be retrofitted to an existing arm (2, 40) or other fixture. Still other variations of rail (4), including but not limited to modifications, substitutions, and supplements, will be apparent to those of ordinary skill in the art.

FIGS. 3A through 7 depict various exemplary embodiments of attachment assemblies (20A through 20E) that may be mounted to rail (4) or elsewhere. Each of these attachment assemblies (20A through 20E) comprises a pair of opposing jaw members (22A through 22E), a jaw knob (24A through 24E), and at least one accessory interface (26A through 26E). Each jaw pair (22A through 22E) comprises a first jaw member (28A through 28E) and a second jaw member (30A through 30E). In each of these examples, each second jaw member (30A through 30E) is selectively moveable toward and away from the first jaw member (28A through 28E). Of course, any jaw pair (22A through 22E) may be configured to open and close in any other fashion.

In one present example illustrated in FIGS. 3A through 7, jaw pair (22A through 22E) may be selectively opened and closed by turning jaw knob (24A through 24E). In other words, jaw knob (24A through 24E) is operable to move at least one movable jaw member (30A through 30E) relative to the other jaw member (28A through 28E), such that the jaw pair (22A through 22E) opens when jaw knob (24A through 24E) is turned for example, counter-clockwise, and closes when jaw knob (24A through 24C) is turned for example, clockwise. Of course, opening and closing of jaw pair (22A through 22E) may be effected by counter-clockwise and clockwise rotation, respectively, of jaw knob (24A through 24E). In the present example, jaw knob (24A through 24E) is operable to effect opening and closing of jaw pair (22A through 22E) by action of a screw assembly (31A through 31C), which is operably coupled with jaw knob (24A through 24E). In one embodiment, screw assembly (31A through 31C) comprises one or more threaded members. In the present example, it will be appreciated that, upon rotation of jaw knob (24A through 24E), which is operatively coupled to screw assembly (31A through 31C), screw assembly (31A through 31C) translates axial force and movement to connector pin (33A through 33C), which effects rotational movement of jaw (30A through 30E) about hinge pin (32A through 32E). This causes jaw member (30A through 30E) to move toward or away from jaw member (28A through 28E), thus closing or opening jaw pair (22A through 22E), respectively.

Those of ordinary skill in the art will appreciate that a variety of alternative mechanisms or means for selectively opening and closing jaw pair (22A through 22E) may be used. For example, in place of jaw knob (24A through 24E) and screw assembly (31A through 31C) of the present example, a lever and/or cam mechanism may be used. For instance, in one embodiment (not shown), a lever, operable by the user, is coupled to a cam and a rod, which is in turn be coupled to the connector pin (33A through 33C), such that movement of the lever by the user will rotate the cam and, selectively, axially pull on the rod or release the rod so as to close or allow opening of the jaw pair (22A through 22E).

In another embodiment (not depicted) of an attachment assembly, a screw assembly is operable to move a jaw pair axially relative to the attachment assembly. In this embodiment, two opposing, movable jaw members of the jaw pair are joined by a connector pin, and are each configured to rotate relative to the connector pin. The jaw pair is resiliently urged to open, such as by a spring or other resilient member(s). The attachment assembly of this example further comprises one or more cam surfaces adjacent to the outer surface of each jaw member, which is/are configured to act as a cam when engaged with the jaw pair. In particular, the cam surface is configured to urge the jaw members to a closed position when the jaw pair is axially retracted by the screw assembly (e.g., when the screw assembly effects pulling on the connector pin joining the jaw members). Accordingly, the jaw members are urged opened by a resilient member when the jaw pair is axially advanced by the screw assembly (e.g., when the screw assembly effects pushing on the connector pin joining the jaw members); while the jaw members are urged closed by the cam surface(s) when the jaw pair is axially retracted by the screw assembly.

Of course, any other mechanism or configuration for opening and/or closing jaw pair (22A through 22E) may be used, several other different embodiments of which will be apparent to those of ordinary skill in the art.

In the present example, when jaw pair (22A through 22E) is in an open position, the attachment assembly (20A through 20E) may be placed onto and moved to a selected position on, or removed from, rail (4). In a closed position, jaw pair (22A through 22E) is configured to grip rail (4), such that attachment assembly (20A through 20E) is suitably attached to rail (4). Accordingly, in the present example, jaw pair (22A through 22E) engages sidewalls (8) of rail (4) at the recessed portions of sidewalls (8) adjacent flange (10). Other suitable interfaces and interacting geometries between jaw pair (22A through 22E) and a rail (4) will be apparent to those of ordinary skill in the art.

In the present example, each jaw member (28A through 28E, 30A through 30E) has a cross section configured to interact with or compliment the cross section of rail (4). In other words, jaw pair (22A through 22E) is configured to interact with or compliment rail (4), such that jaw pair (22A through 22E) may securely grip rail (4). Attachment assembly (20A through 20E) may thus be positioned as desired along rail (4) with jaw pair (22A through 22E) generally opened; and then jaw pair (22A through 22E) may be closed upon rail (4) to secure attachment assembly (20A through 20E) to rail (4). It will be appreciated that attachment assembly (20A through 20E) may thus be brought into initial engagement with rail (4) in a direction of movement transverse to rail (4). In other words, particularly given the opening and closing of jaw pair (22A through 22E), it need not be necessary to slide attachment assembly (20A through 20E) of the present example onto an end of rail (4) in a longitudinal movement to effect engagement. Of course, the cross section of jaw members (28A through 28C, 30A through 30C) need not mirror, trace, or otherwise compliment the cross section of rail (4), and any other suitable cross sections may be used for jaw members (28A through 28C, 30A through 30C) and/or rail (4).

In one embodiment, one portion of the attachment assembly (20A through 20E) is configured to be selectively rotatable and securable in selected rotational positions relative to the remaining portion of the attachment assembly (20A through 20E). Where such rotation is permitted, the attachment assembly (20A through 20E) may further include a locking mechanism or other mechanism operable to selectively permit or prevent such rotation. For example, referring to FIGS. 3A through 4C, 6, and 7, a body portion (34A, 34B, 34D, 34E) of attachment assembly (20A, 20B, 20D, 20E) is configured to be selectively rotatable and securable in selected rotational positions relative to jaw pair (22A, 22B, 22D, 22E) portion. Each of body portion (34A, 34B, 34D, 34E) and jaw pair (22A, 22B, 22D, 22E) portion is formed to have cooperating features, such as cooperating starburst features (not shown), at interface (35A, 35B, 35D, 35E) with jaw pair (22A, 22B, 22D, 22E) portion.

Upon loosening of screw assembly (31A, 31B), or other suitable drawing and holding mechanism, spatial clearance between body portion (34A, 34B, 34D, 34E) and jaw pair (22A, 22B, 22D, 22E) portions may be provided at interface (35A, 35B, 35D, 35E), enabling disengagement of respective cooperating features on each of body portion (34A, 34B, 34D, 34E) and jaw pair (22A, 22B, 22D, 22E) portion, and thereby enabling rotation of body portion (34A, 34B, 34D, 34E) with respect to jaw pair (22A, 22B, 22D, 22E) portion about the axis of screw assembly (31A, 31B) (or other suitable drawing and holding mechanism), and vice versa. Conversely, upon tightening of screw assembly (31A, 31B) or other suitable drawing and holding mechanism, body portion (34A, 34B, 34D, 34E) and jaw pair (22A, 22B, 22D, 22E) portion are drawn together, engaging respective cooperating features on each of body portion (34A, 34B, 34D, 34E) and jaw pair (22A, 22B, 22D, 22E) portion at interface (35A, 35B, 35D, 35E), and thereby preventing rotation of body portion (34A, 34B, 34D, 34E) with respect to jaw pair (22A, 22B, 22D, 22E) portion, and vice versa.

Those of ordinary skill in the art will appreciate that there may be a variety of other suitable mechanisms that may be substituted for the screw assembly to serve as the drawing and holding mechanism described in the preceding paragraph. For instance, the previously-described lever and cam mechanism may be used. That is, a lever, operable by the user, may be coupled to a cam and a rod, which may be in turn be coupled to the connector pin (33A and 33B), such that movement of the lever by the user will rotate the cam and, selectively, axially pull on the rod or release the rod so as to draw respective starburst features on each of body portion (34A, 34B, 34D, 34E) and jaw pair (22A, 22B, 22D, 22E) portions at interface (35A, 35B, 35D, 35E) together, or allow them to be disengaged.

It will be apparent to those of ordinary skill in the art that attachment assemblies (20A, 20B, 20D, 20E) are operable to be clamped to rail (4) and rotationally adjusted (i.e., body portion (34A, 34B, 34D, 34E) rotatably adjusted relative to jaw pair (22A, 22B, 22D, 22E) portion) substantially simultaneously. In the present example, the same mechanism that effects clamping of jaw pair (22A, 22B, 22D, 22E) permits rotation of body portion (34A, 34B, 34D, 34E) relative to jaw pair (22A, 22B, 22D, 22E) portion. Alternatively, separate mechanisms may be used to clamp jaw pair (22A, 22B, 22D, 22E) and permit rotation of body portion (34A, 34B, 34D, 34E) relative to jaw pair (22A, 22B, 22D, 22E) portion. In other words, enablement of simultaneous clamping and rotational adjustment is not required, though it may be employed.

In yet another embodiment, the same mechanism that effects clamping of jaw pair (22A, 22B, 22D, 22E) permits rotation of body portion (34A, 34B, 34D, 34E) relative to jaw pair (22A, 22B, 22D, 22E) portion, yet one or more additional features is/are provided to selectively prevent one of clamping or rotation while the other of clamping or rotation is permitted. For instance, a lever, tab, pin, switch, or other feature may be provided to prevent rotation of body portion (34A, 34B, 34D, 34E) relative to jaw pair (22A, 22B, 22D, 22E) portion during clamping of jaw pair (22A, 22B, 22D, 22E) to rail (4). The same feature (or another feature) may be operable to selectively prevent un-clamping of an attachment assembly (20A through 20E) that is clamped to a rail (4), while body portion (34A, 34B, 34D, 34E) is permitted to rotate relative to jaw pair (22A, 22B, 22D, 22E) portion.

Still other suitable relationships between clamping of jaw pair (22A, 22B, 22D, 22E) and rotation of body portion (34A, 34B, 34D, 34E) relative to jaw pair (22A, 22B, 22D, 22E) portion, as well as structures, mechanisms, and configurations for providing such relationships, will be apparent to those of ordinary skill in the art.

Each attachment assembly (20A through 20E) of the present example further comprises an accessory interface (26A through 26E). Each accessory interface (26A through 26E) is configured to receive and immovably secure an accessory suitably configured with features to cooperate therewith. In one embodiment, accessory interface (26A through 26E) is configured to provide a way for accessories to be mounted thereto, where such accessories could not otherwise be easily mounted to rail (4). In this embodiment, a suitably configured accessory may be mounted to accessory interface (26A through 26E). In the present example, each accessory interface (26A through 26E) comprises a starburst feature that is configured to cooperate with or otherwise securably engage with a complimentary and suitably configured starburst feature on a mountable accessory. Accessory interface (26A through 26E) may also comprise an accessory bolt (36A) or other suitable attachment mechanism that may be used to hold a suitably configured accessory attached and in place at the accessory interface (26A through 26E). When used, bolt (36A) may comprise a knob (37A) or other feature operable to turn bolt (36A). In one embodiment, at least a portion of bolt (36A) is threaded. Of course, any other configuration for bolt (36A) may be used.

It will be appreciated that embodiments of attachment assemblies (20A, 20B, 20D, 20E) may permit rotation of instruments secured thereto in at least two planes. For instance, where an instrument (not shown) is engaged with accessory interface (26A, 26B, 26D, 26E), the instrument may be rotated, relative to body portion (34A, 34B, 34D, 34E), to a selected position. Accessory interface (26A, 26B, 26D, 26E) thus provides a first plane of rotation for positioning or other purposes. With the instrument rotationally positioned relative to body portion (34A, 34B, 34D, 34E) and secured thereto, body portion (34A, 34B, 34D, 34E) may be rotated relative to jaw pair (22A, 22B, 22D, 22E) portion for further positioning of the instrument. Interface (35A, 35B, 35D, 35E) thus provides a second plane of rotation for positioning or other purposes. Of course, it will be appreciated that more or fewer planes of rotation may be provided. In addition, while the two planes of rotation in the present example are generally perpendicular, it will be appreciated that any other relative orientation of rotational planes may be used. Variations for providing alternate planes of rotation will be apparent to those of ordinary skill in the art. Alternatively, rotation may be restricted or not permitted by suitable configurations.

Figure 6:
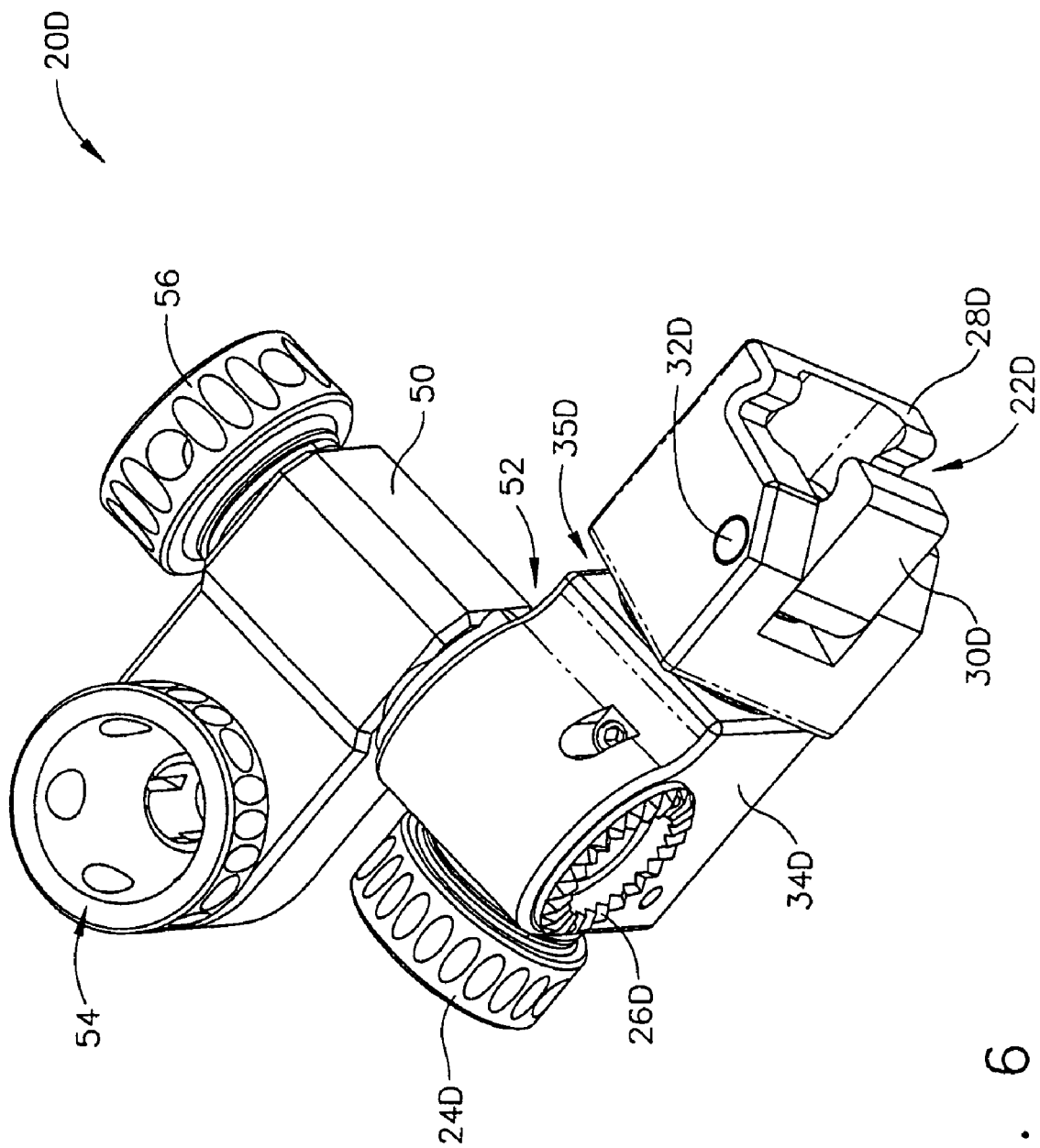
FIG. 6 depicts a perspective view of an alternative attachment assembly.

One exemplary variation providing additional planes of rotation is depicted in FIG. 6. The attachment assembly (20D) of FIG. 6 further comprises a mounting member (50) coupled with body portion (34D) at interface (52). Interface (52) comprises starburst features similar to the starburst features of interface (35D). Mounting member (50) further comprises a knob (56), which operates in a fashion similar to knob (24D).

That is, knob (56) is operable to selectively permit separation of mounting member (50) from body portion (34D) at interface (52) (e.g., when turned counter-clockwise), and to bring mounting member (50) and body portion (34D) together at interface (52) (e.g., when turned clockwise). With mounting member (50) suitable separated from or otherwise suitable disengaged with body portion (34D), mounting member (50) may be rotated to a variety of orientations relative to body portion (34D). In addition, just as starburst features of interface (35D) are configured to prevent rotation of body portion (34D) relative to jaw pair (22D) portion when those starburst features are engaged; starburst features of interface (52) are configured to prevent rotation of mounting member (50) relative to body portion (34D) when those starburst features are engaged. Of course, any other features may be provided at interface (52), as well as any substitute for knob (56). Mounting member (50) further comprises an accessory mount (54), to which a variety of accessories may be mounted in any suitable fashion (e.g., via screwing, clamping, clipping, etc.). Accessory mount (54) is configured to provide yet another plane of rotation. That is, an accessory may be rotated relative to mounting member (50) to any suitable position prior to or after coupling of the accessory with accessory mount (54). Accessory mount (54) may further be configured to selectively secure an accessory to mounting member (50) (e.g., selectively preventing further rotation of the accessory relative to mounting member (50)). Still other variations for attachment assembly (20D) will be apparent to those of ordinary skill in the art.

Figure 7:
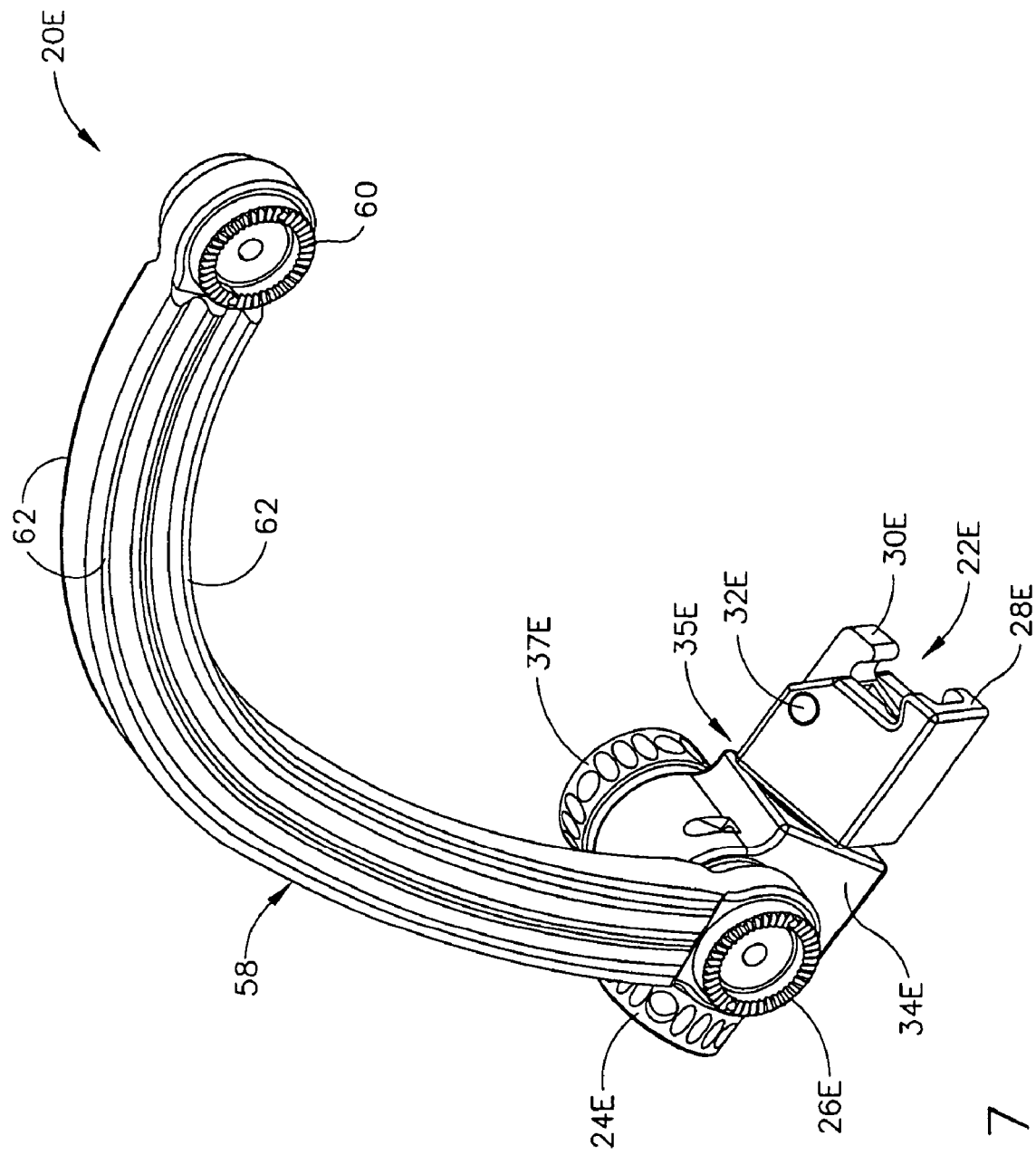
FIG. 7 depicts a perspective view of an alternative attachment assembly.

In the embodiment depicted in FIG. 7, attachment assembly (20E) comprises a J-arm (58) coupled with attachment assembly (20E). In this embodiment, attachment assembly (35E) is essentially the same as attachment assembly (20A) shown in FIGS. 3A through 3D. Of course, attachment assembly (20E) may be varied. J-arm (58) of the present example provides accessory interface (26E), as well as an additional accessory interface (60), which is structurally similar to accessory interface (26A through 26E). A variety of accessories may thus be mounted to accessory interface (60), such as those listed below and others that will be apparent to those of ordinary skill in the art. J-arm (58) further comprises ribs (62) along its perimeter. Each pair of ribs (62) is similar to rail (4) in that they are configured to receive jaw pairs (22A through 22D). In other words, jaw pairs (22A through 22D), as well as a variety of other structures, may be secured to J-arm (58) by clamping of jaw pairs (22A through 22D) on or about one or more of ribs (62).

Attachment assembly (20E) further comprises a knob (37E). Knob (37E) in this example is operable to selectively secure J-arm (58) to body portion (34E) (e.g., through clockwise rotation of knob (37E)). Knob (37E) is further operable to loosen J-arm (58) relative to body portion (34E) (e.g., through counter-clockwise rotation of knob (37E)). With J-arm (58) loosened relative to body portion (34E), J-arm (58) may be rotated relative to body portion (34E) to any suitable orientation. As used herein, the term "loosened" includes configurations where J-arm (58) is completely separated from body portion (34E), where J-arm (58) is still connected to body portion (34E) yet rotatable relative thereto, and other configurations as will be apparent to those of ordinary skill in the art. Of course, any variation, substitute, or supplement of knob (37E) may be used, as may any other relationship between J-arm (58) and body portion (34E).

While J-arm (58) is shown as having a generally "J"-shaped configuration, it will be appreciated that any other configuration may be used. By way of example only, J-arm (58) may be "L"-shaped, generally straight, zig-zagged, malleable, or have any other properties or configuration. In another embodiment, J-arm (58) is substituted or supplemented with a halo retractor (not illustrated). Of course, any other component, device, etc. may be used to substitute or supplement J-arm (58). Still other ways in which attachment assembly (20D) may be varied will be apparent to those of ordinary skill in the art.

In another embodiment, arms (2, 40) and/or attachment assemblies (20A through 20E) include one or more features configured to provide dampening of vibrations. Various embodiments of such features will be apparent to those of ordinary skill in the art.

Those of ordinary skill in the art will appreciate that a variety of accessories may be mounted to rail (4) of the present example using a jaw pair (22A through 22E) of the present example. Similarly, those of ordinary skill in the art will appreciate that a variety of accessories may be mounted to an attachment assembly (20A through 20E) of the present example. Such accessories may include, but are certainly not limited to, a halo, a halo retractor, a halo support rod/frame/bracket/member, a J-arm, a J-arm retractor system, a flexible arm, an endoscope, a navigation star for an infra-red camera or other image-guided fiducial marker, flexible retractor arms, retractor blades, brackets, trays, support rods, skull pins, skull pin holding fixtures, head rests, pads, biopsy needles, spatulas, and the like. Still other accessories suitable for mounting to rail (4) and/or attachment assembly (20A through 20E) will be apparent to those of ordinary skill in the art. In addition, it will be appreciated that attachment assemblies (20A through 20E) and/or jaw pairs (22A through 22E) may be secured to a variety of structures other than arms (2, 40) and/or rail (4).

It will also be appreciated that the illustrative embodiments of attachment assemblies (20A through 20E) illustrated in FIGS. 3A through 7 are non-exhaustive, and that a variety of other structures or mechanisms may comprise a jaw pair (22A through 22E) for mounting to rail (4). Attachment assemblies (20A through 20E) may each be constructed such that they may securably accommodate a variety of instruments or accessories. Alternatively, attachment assemblies (20A through 20E) may be constructed with a dedicated configuration to only accommodate a certain instrument/accessory, a certain type or class of instrument/accessory, or a certain range of instruments/accessories. In addition, any other suitable configuration for a jaw pair (22A through 22E) may be used to mount a fixture, object, variation of attachment assemblies (20A through 20E), or accessory to rail (4).

In the present example, rail (4), first jaw member (28A through 28E), second jaw member (30A through 30E), attachment assembly (20A through 20E), and body portion (34A, 34B, 34D, 34E) each comprise cast and/or machined aluminum. Of course, any suitable materials may be used. By way of example only, any of these components, or portions thereof, may be made from any suitable metals or polymers or other materials now or hereafter known as suitable for use for surgical fixture components, and combinations thereof, having desired strength, hardness, wear resistance, and, if desired, radiolucent properties, as will be apparent to those of ordinary skill in the art. By way of example only, these components, or portions thereof, may be made from aluminum or alloys thereof, steel, stainless steel, other metals and metal alloys, carbon fiber, plastics or polymers including but not limited to PEEK (a product produced by Victrex PLC of the United Kingdom), POM (polyacetal, polyoxymethylene), phenolic-fiber laminates or epoxy-fiber laminates (such as the product currently known as "NOVOTEX," by way of example only). Still other suitable materials, including combinations thereof, will be apparent to those of ordinary skill in the art.

In the present example, screws (12A through 12E), jaw knob (24A through 24E), screw assembly (31A through 31C), hinge pin (32A through 32E), connector pin (33A through 33C) and connector bolt (35A) are made of stainless steel. Of course, any other material or combinations of materials may be used, including but not limited to those listed above.

Having shown and described various embodiments and concepts of the invention, further adaptations of the methods and systems described herein can be accomplished by appropriate modifications by one of ordinary skill in the art without departing from the scope of the invention. Several of such potential alternatives, modifications, and variations have been mentioned, and others will be apparent to those skilled in the art in light of the foregoing teachings. Accordingly, the invention is intended to embrace all such alternatives, modifications and variations as may fall within the spirit and scope of the appended claims and is understood not to be limited to the details of structure and operation shown and described in the specification and drawings.

What is claimed is:

1. A skull clamp system, comprising:
   (a) a pair of arms defining a skull clamp, wherein each of the arms comprise:
      (i) an outer face defining a profile,
      (ii) a first end configured to receive one or more cranial stabilizing components, and
      (iii) a second end opposite the first end, wherein the second end of one of the arms is configured to securely and adjustably insert into the second end of the other of the arms;
   (b) a rail secured to the outer face of a selected one of the arms and conforming to the profile of the selected one of the arms, wherein the rail comprises
      recessed sidewalls extending longitudinally along the rail, wherein the recessed sidewalls define a pair of grooves; and
   (c) an accessory attachment assembly comprising a pair of jaws, wherein at least one of the jaws is configured to pivot toward the other of the jaws, wherein the jaws are configured to grip the rail at a selected point along the pair of grooves.

2. The skull clamp system of claim 1, wherein the accessory attachment assembly further comprises:
   (a) a gripping mechanism comprising:
      (i) a first jaw having a first gripping portion, and
      (ii) a second jaw having a second gripping portion;
         wherein the second jaw is moveably connected to the first jaw,
         whereby the second gripping portion is operable to be selectively moved toward or away from the first gripping portion to close or open, respectively, the gripping mechanism thereby engaging and gripping the surgical fixture;
   (b) an accessory attachment mechanism moveably coupled with the gripping mechanism, wherein the accessory attachment mechanism comprises an accessory interface portion configured to receive an accessory and to provide a plane of rotation for positioning the accessory relative to the surgical fixture; and
   (c) an actuating member, wherein the actuating member is in mechanical communication with the gripping mechanism and with the accessory attachment mechanism, and wherein the actuating member is operable by a user to effect at least one of:

(i) substantially simultaneous closing of the gripping mechanism and fixation of the accessory attachment mechanism relative to the gripping mechanism, or (ii) substantially simultaneous opening of the gripping mechanism and release of fixation of the accessory attachment mechanism relative to the gripping mechanism.

3. The attachment assembly of claim 2, further comprising a housing, wherein the first jaw is integral with the housing.

4. The attachment assembly of claim 3, wherein the second jaw is pivotally secured to the housing.

5. The attachment assembly of claim 2, wherein the second gripping portion is configured to rotate toward the first gripping portion.

6. The attachment assembly of claim 2, further comprising an accessory attached to the accessory interface portion.

7. The attachment assembly of claim 2, wherein the accessory attachment mechanism is operable to selectively rotate relative to the gripping mechanism.

8. The attachment assembly of claim 2, wherein the gripping mechanism and the accessory attachment mechanism are operable to be selectively engaged at an interface.

9. The attachment assembly of claim 2, wherein the actuating member comprises a knob.

10. The attachment assembly of claim 9, wherein the actuating member further comprises a screw member, wherein the screw member is configured to translate rotational motion of the knob into axial motion of a portion of the gripping mechanism.

11. The attachment assembly of claim 2, wherein the actuating member is operable to draw the gripping mechanism toward the accessory attachment mechanism.

12. The skull clamp system of claim 1, wherein the pair of arms join to form a generally u-shaped skull clamp.

13. The skull clamp system of claim 1, wherein the rail is secured to the selected one of the arms with one or more fasteners.

14. The skull clamp system of claim 1, wherein each arm of the pair of arms comprises a rail, wherein at least one of the rails has a cross-section comprising a "T" shape or a dovetail shape.

15. The skull clamp system of claim 1, wherein the second end of one of the arms comprises a slot, wherein the slot is configured to receive the second end of the other one of the arms.

16. The skull clamp system of claim 1, wherein the rail is integrally formed with the selected one of the arms.

17. The skull clamp system of claim 1, wherein the outer face defines an arcuate profile, and wherein the rail conforms to the arcuate profile.

18. The skull clamp system of claim 1, wherein the outer face defines a first width representing the maximum width of the arm, wherein the rail comprises an outer face defining a second width representing the maximum width of the rail, and wherein the second width is less than the first width.

19. An assembly providing at least three axes of rotational adjustment for attaching accessories to a surgical fixture having a rail comprising a pair of grooves and a flange, the assembly comprising:

(a) a gripping portion, wherein the gripping portion comprises a pair of jaws, wherein the jaws are operable to grip the rail along the pair of grooves and flange of the rail;

(b) an intermediate portion moveably coupled with the gripping portion, wherein the intermediate portion comprises a feature configured to selectively fix the intermediate portion to the gripping portion, wherein the feature is further configured to selectively permit rotation of the intermediate portion relative to the gripping portion about a first axis of rotation; and (c) an accessory attachment portion moveably coupled with the intermediate portion, wherein the accessory attachment portion comprises a first feature configured to selectively fix the accessory attachment portion to the intermediate portion, wherein the first feature is further configured to selectively permit rotation of the accessory attachment portion relative to the intermediate portion about a second axis of rotation, wherein the accessory attachment portion is configured to receive a surgical accessory, wherein the accessory attachment portion comprises a second feature configured to selectively fix the surgical accessory relative to the accessory attachment portion, wherein the second feature is further configured to selectively permit rotation of the surgical accessory relative to the accessory attachment portion about a third axis of rotation.

20. The attachment assembly of claim 19, wherein the intermediate portion is configured to receive a surgical accessory, wherein the intermediate portion comprises a feature configured to secure the surgical accessory relative to the intermediate portion, wherein the feature is further configured to selectively permit rotation of the surgical accessory relative to the intermediate portion about a fourth axis of rotation.

21. The attachment assembly of claim 19 further comprising an elongated arm portion moveably coupled with the accessory attachment portion, wherein the elongated arm portion comprises:

(a) at least one accessory interface for securing a surgical accessory; and (b) at least one set of ribs configured to adjustably receive a clamping member.

* * * * *